US008521445B2

(12) United States Patent
Snelling et al.

(10) Patent No.: US 8,521,445 B2
(45) Date of Patent: Aug. 27, 2013

(54) CORROSION RATE MONITORING

(75) Inventors: Ricky Eugene Snelling, Tulsa, OK (US); Donald Ray Engelbert, Copan, OK (US); Omar Jesus Yepez, Stillwater, OK (US)

(73) Assignee: ConocoPhillips Company, Houston, TX (US)

( * ) Notice: Subject to any disclaimer, the term of this patent is extended or adjusted under 35 U.S.C. 154(b) by 302 days.

(21) Appl. No.: 12/873,775

(22) Filed: Sep. 1, 2010

(65) Prior Publication Data

US 2011/0066388 A1 Mar. 17, 2011

Related U.S. Application Data

(60) Provisional application No. 61/243,450, filed on Sep. 17, 2009.

(51) Int. Cl.
*G07C 3/00* (2006.01)
*G05B 19/4065* (2006.01)

(52) U.S. Cl.
USPC .................. 702/34; 422/53; 436/6; 436/151; 356/237.2; 250/301; 250/341.1; 73/104

(58) Field of Classification Search
USPC ................ 702/30, 33, 34, 35, 113, 182–185, 702/127; 436/6
See application file for complete search history.

(56) References Cited

U.S. PATENT DOCUMENTS 2,963,349 A * 12/1960 Bernard et al. .................. 436/6
4,056,445 A 11/1977 Gauntt et al.
4,130,464 A 12/1978 Kanno et al.
4,387,041 A 6/1983 Hort et al.
4,387,042 A 6/1983 Hort et al.
4,388,206 A 6/1983 Hort et al.
4,419,266 A 12/1983 Hort et al.
4,448,710 A 5/1984 Hort et al.
4,627,905 A 12/1986 Garner et al.
4,683,035 A * 7/1987 Hunt et al. .................... 205/777
4,758,312 A * 7/1988 Hunt et al. .................... 205/777

(Continued)

FOREIGN PATENT DOCUMENTS

CN 201107255 8/2008
WO WO 2008120236 A2 * 10/2008
WO WO2008122989 10/2008

OTHER PUBLICATIONS

Edmondson and Rue, "Wet H2S Corrosion and Inhibition," 1991 NPRA Annual Meeting, Mar. 17-19, Convention Center, San Antonio, TX (1991).

(Continued)

*Primary Examiner* — Jonathan C Teixeira Moffat
*Assistant Examiner* — Stephanie Chang
(74) *Attorney, Agent, or Firm* — ConocoPhillips Company

(57) ABSTRACT

Methods and apparatus relate to measuring corrosion rate. Flowing corrosive fluid contacts a metal coupon or object and results in an effluent stream. The effluent stream contains metal from the object due to reaction of constituents in the fluid with the metal. Analysis of the effluent stream measures concentration of the metal therein. Since the concentration of the metal in the effluent stream is indicative of mass loss from the object, calculations provide the corrosion rate utilizing weight of the metal that is eluted, surface area of the object and exposure time of the object with the corrosive fluid.

15 Claims, 2 Drawing Sheets

103
AUTOCLAVE
110
112
102
109
111
100
104
FLUID TANK
ANALYZER
108
114
106
PROCESSOR

(56) References Cited

U.S. PATENT DOCUMENTS

| | | | | |
|---|---|---|---|---|
| 5,219,542 | A * | 6/1993 | Lowery et al. | 423/230 |
| 5,531,103 | A * | 7/1996 | Eaton | 73/61.62 |
| 5,914,292 | A * | 6/1999 | Khare et al. | 502/406 |
| 6,294,387 | B1 * | 9/2001 | Yepez et al. | 436/6 |
| 6,869,522 | B2 * | 3/2005 | Khare et al. | 208/299 |
| 7,127,959 | B2 | 10/2006 | Blum et al. | |
| 7,182,918 | B2 * | 2/2007 | Hoover et al. | 422/141 |
| 7,553,449 | B2 * | 6/2009 | Yeganeh et al. | 422/53 |
| 7,854,835 | B2 * | 12/2010 | Hoover et al. | 208/250 |
| 2003/0188993 | A1 * | 10/2003 | Khare et al. | 208/208 R |
| 2006/0063263 | A1 * | 3/2006 | Yeganeh et al. | 436/6 |
| 2009/0238811 | A1 * | 9/2009 | McDaniel et al. | 424/94.2 |
| 2009/0283448 | A1 * | 11/2009 | Hoover et al. | 208/243 |
| 2010/0126842 | A1 * | 5/2010 | Subramaniyam | 203/7 |
| 2011/0066388 | A1 * | 3/2011 | Snelling et al. | 702/30 |
| 2011/0067497 | A1 * | 3/2011 | Grubb et al. | 73/623 |
| 2012/0075629 | A1 * | 3/2012 | Yepez et al. | 356/336 |
| 2012/0298555 | A1 * | 11/2012 | Uppili et al. | 208/113 |

OTHER PUBLICATIONS

Dorsey, et al. "Monitoring for Corrosion and Microbiological Activity in a Cooling Water System", CORROSION/2002, NACE, Houston or PPChem, December abstracts (2002).

Smith & Jootsen, "Corrosion of Carbon Steel by H2S in CO2 Containing Oilfield Environments," ConocoPhillips (2005).

Achour, Kolts, and Joosten, "Experimental Study of Under Deposit Corrosion (UDC) in Presence of Iron Sulfide," ConocoPhillips (2007).

* cited by examiner

CORROSION RATE MONITORING

CROSS-REFERENCE TO RELATED APPLICATION

This application is a non-provisional application which claims benefit under 35 USC §119(e) to U.S. Provisional Application Ser. No. 61/243,450 filed Sep. 17, 2009, entitled "CORROSION RATE MONITORING," which is incorporated herein in its entirety.

STATEMENT REGARDING FEDERALLY SPONSORED RESEARCH OR DEVELOPMENT

None

FIELD OF THE INVENTION

Embodiments of the invention relate to methods and systems for corrosion rate monitoring.

BACKGROUND OF THE INVENTION

Various applications benefit from knowledge regarding corrosiveness of certain fluids on particular metals. Experiments can test to determine such corrosion rates. By way of example, the corrosion rates facilitate selecting which oils to accept for processing in refineries, evaluating corrosion inhibiting additives, and scheduling replacement for components that are susceptible to corrosion.

Gravimetric analysis of metal coupons provides one past experimentation technique used to determine the corrosion rates. However, handling and processing of the coupons to obtain final weight measurements at an end of a test run for comparison to an initial weight introduces potential for errors especially since these weight differences may represent about one percent or even less of the initial weight of the coupon. The gravimetric analysis also yields only one data point per test run that may last several days and include time consuming setup of an autoclave. Dividing the test run to obtain more data points thus becomes impractical due to inefficiency in repeated cooling, cleaning, drying and weighing of the coupon along with purging, pressurizing and heating to reset the autoclave for each additional data point. Having the one data point without any data points for comparison both limits confidence in the one data point and prevents ability to evaluate adjustments in process conditions throughout a single test run.

Therefore, a need exists for improved methods and systems for corrosion rate monitoring.

SUMMARY OF THE INVENTION

In one embodiment, a method of measuring corrosion rate includes exposing an object made of metal to a flow of corrosive liquid. The corrosive liquid passes into an analysis device after the object is exposed to the corrosive liquid. The method further includes determining a corrosion rate of the metal within the corrosive liquid based on a known surface area of the object and concentration of the metal within the corrosive liquid as measured by the analysis device.

According to one embodiment, a method of measuring corrosion rate includes preparing an autoclave for operation by closing the autoclave for internal pressurization of the autoclave above ambient pressure and heating the autoclave to a reaction temperature. Passing corrosive liquid through the autoclave exposes an object made of metal and disposed in the autoclave to a flow of the corrosive liquid. First and second samples of the corrosive liquid taken respectively from the autoclave during first and second time intervals pass into an analysis device. Even though the second time interval occurs after the first time interval, the autoclave remains closed while the first and second samples are obtained without removing the object from the autoclave. In addition, determining corrosion rates of the metal within the corrosive liquid for the first and second time intervals independent from one another utilizes a known surface area of the object and concentrations of the metal within the corrosive liquid as measured by the analysis device.

For one embodiment, a system for measuring corrosion rate includes a source of corrosive liquid and an object that is made of metal, disposed in a container, and in fluid communication with a flow path of the corrosive liquid. The system further includes an analysis device coupled to receive the corrosive liquid from the container. A processor of the system receives input data including concentration of the metal within the corrosive liquid as measured by the analysis device and is operable to output a corrosion rate of the metal within the corrosive liquid determined based on the input data and a known surface area of the object.

BRIEF DESCRIPTION OF THE DRAWINGS

The invention, together with further advantages thereof, may best be understood by reference to the following description taken in conjunction with the accompanying drawings.

DETAILED DESCRIPTION OF THE INVENTION

Embodiments of the invention relate to methods and systems for measuring corrosion rate. Flowing corrosive fluid contacts a metal coupon or object and results in an effluent stream. The effluent stream contains metal from the object due to reaction of constituents in the fluid with the metal. Analysis of the effluent stream measures concentration of the metal therein. Since the concentration of the metal in the effluent stream is indicative of mass loss from the object, calculations provide the corrosion rate utilizing weight of the metal that is eluted, surface area of the object and exposure time of the corrosive fluid with the object. For some embodiments, the corrosion rate enables selection of oils to accept for processing in a refinery, evaluation of a corrosion inhibiting additive, or determination of criteria, such as material type or replacement timing, for components susceptible to corrosion.

Figure 1:
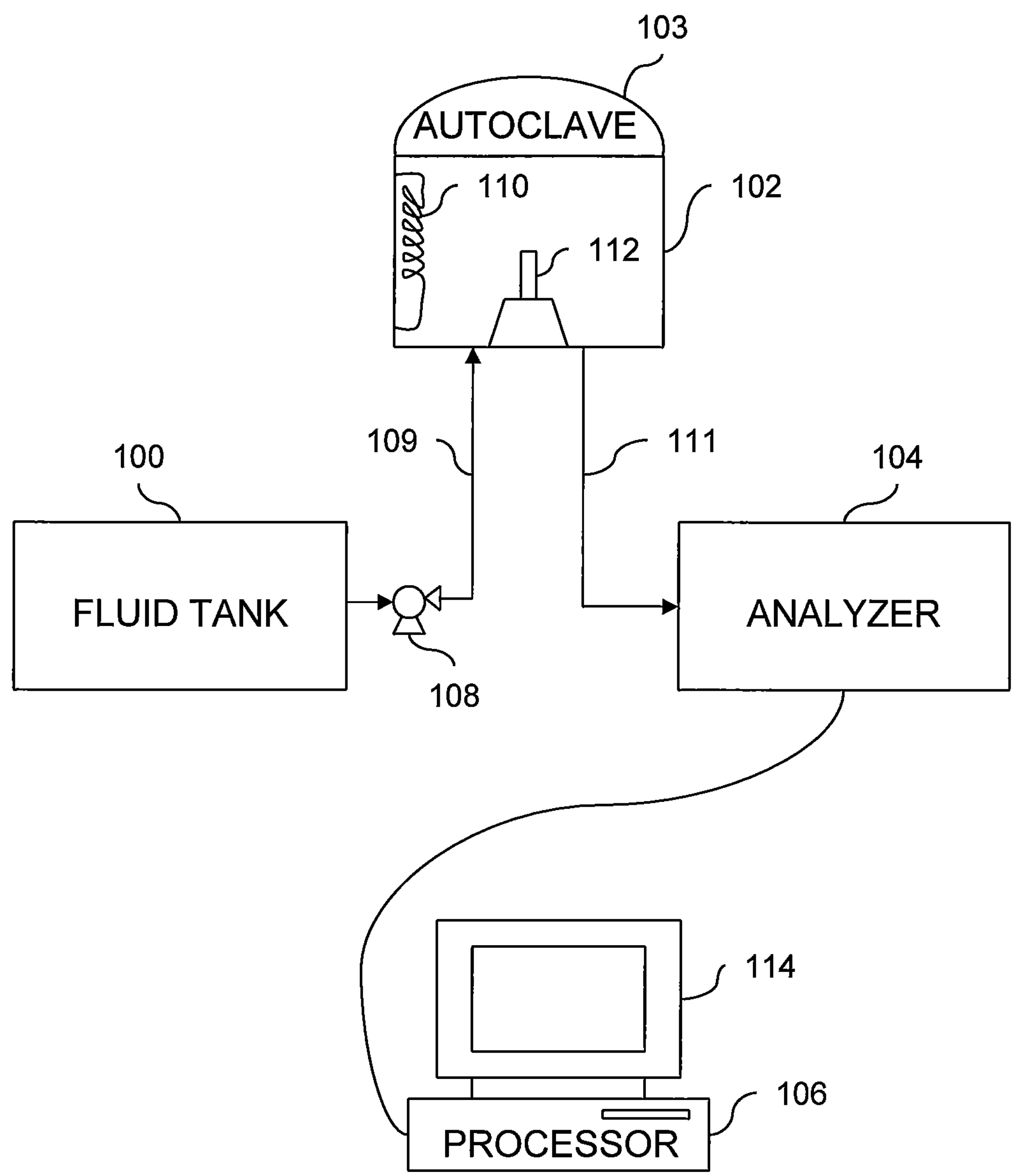
FIG. 1 is a schematic of a system that includes a flow-through autoclave and effluent analyzer and is operable to measure corrosion rate of a metal coupon in the autoclave, according to one embodiment of the invention.

FIG. 1 shows an exemplary testing system for measuring corrosion rate and that includes a supply of corrosive liquid in a fluid tank 100, an autoclave 102 coupled to receive the liquid from the tank 100, an analysis device 104 of the liquid from the autoclave 102 and an optional processor 106 of data input from the analysis device 104. A lid 103 of the autoclave 102 closes an interior volume of the autoclave 102 from an external environment. In operation, a pump 108 in some embodiments disposed along a feed line 109 that couples the tank 100 and the autoclave 102 pressurizes the liquid that passes through the autoclave 102. For some embodiments, a heater 110 maintains the liquid within the interior volume of the autoclave at a desired temperature such that temperature of the liquid in addition to pressure of the liquid inside the autoclave 102 may be above ambient. The heater 110 schematically depicted in the interior volume of the autoclave 102 may supply heat to the liquid while located outside of the autoclave 102.

Prior to operation with the autoclave 102 closed, the lid 103 of the autoclave 102 while opened enables placement of a metal object 112 in the interior volume of the autoclave 102. The object 112 contacts the liquid as the liquid passes through the autoclave 102 and may be retained in position within the autoclave 102 by a support or holder. The liquid flows through the autoclave 102 throughout operation and thus exits the autoclave via effluent stream 111 after having contacted the object 112. At least some of the liquid from the effluent stream 111 passes into the analysis device 104.

The analysis device 104 measures concentration of one or more metals in the liquid from the effluent stream 111. For some embodiments, an inductively coupled plasma (ICP) atomic emission spectrometer provides the analysis device 104. Other suitable examples of the analysis device 104 may rely on atomic absorption spectroscopy, titration, or addition of a colorimetric agent reactive with the metal prior to use of a spectrophotometer.

In some embodiments, the analysis device 104 sends input data based on the concentration of the metal measured to the processor 106. The processor 106 forms part of a computer and defines logic stored on computer readable memory and configured to perform operations as described herein with respect to determining of corrosion rate. An output 114, such as a printer or display, provides the corrosion rate to a user.

The testing system even though shown simplified may incorporate other optional details, which include an inert fluid purge, such as nitrogen, input into the autoclave 102 prior to the liquid from the tank 100. In addition, agitation of the liquid in the interior volume of the autoclave 102 may enhance contact between the liquid and the object 112. For example, the autoclave 102 may include a stirrer disposed within the liquid in the interior volume of the autoclave 102.

The liquid flows through the autoclave 102 during operation to facilitate preventing thermal degradation of constituents, such as oil, naphthenic acids and/or sulfur compounds, within the liquid. While other testing techniques utilizing powder particles may have relative shorter operational durations, contact of the object 112 with the liquid may last for at least about 12 hours, at least about a day, or at least about 3 days. Over this time such undesired degradation and even coking of the oil can occur for batch processes that do not allow for flow-through of the liquid during operation.

The metal for which the concentration is measured by the analysis device 104 forms the object 112 placed in the autoclave 102 since chemical attack due to reaction of the liquid with the metal of the object 112 causes the effluent stream 111 to contain some of the metal from the object 112. In some embodiments, at least one of iron, manganese, molybdenum and nickel provide the metal that forms the object 112. The metal as used herein may refer to elemental metals or compounds containing metals, such as oxidized metals within the effluent stream 111.

In comparison to separation techniques such as filtering required with the testing that uses the powder particles, size of the object 112 facilitates holding of the object 112 within the autoclave 102 without requiring additional handling or processing of the object 112 to remove the effluent stream 111. For some embodiments, the object 112 defines a singular continuous mass with a surface area greater than about 5 square centimeters ($cm^2$) or between about 5 $cm^2$ and about 25 $cm^2$ and may hence be disposed alone or in multiples (e.g., 2-10) within the autoclave 102 during operation. The size and shape of the object 112 makes direct measurement of the surface area possible unlike the powder particles in which the surface area is not definable from measurable dimensions. For example, machine-stamping may create the object 112 with dimensions of about 2.54 cm by about 1.27 cm by about 0.16 cm. While qualitative ranking or calibration back to corresponding coupon tests is possible without knowing the surface area as occurs with the powder particles, calculations described herein can utilize the surface area of the object 112 and obtain the corrosion rates in traditional units of dimension per unit time (e.g., mils/year).

Corrosiveness of the liquid that is contacted with the object 112 may come from acids or bases within the liquid. A mixture of hydrocarbons and naphthenic acids provides an example of the liquid supplied from the tank 100. For example, the naphthenic acids may react with the iron within the object 112 if made from carbon steel.

Processing parameters depend on criteria desired to be tested. In addition to meeting or modeling American Society for Testing and Materials (ASTM) standards, the processing parameters may vary to simulate anticipated conditions of particular applications in which the metal and/or liquid are to be used. The processing parameters may include flow rate for passing the liquid through the autoclave 102, constituents of the liquid, total acid number (TAN) of the liquid, rotation speed of a stirrer in the autoclave 102, pressure of the liquid in the autoclave 102, and temperature of the liquid in the autoclave 102. For example, the temperature and the pressure may range from about 225° C. to about 325° C. and about 2750 kilopascal (kPa) to about 3500 kPa.

A single run may utilize distinct time intervals with different processing parameters for which respective corrosion rates are determined. The "single run" refers to operation of the autoclave 102 as aforementioned without opening the autoclave 102 such that the object 112 remains in the interior volume of the autoclave 102. The autoclave 102 may remain closed while any number of determinations of the corrosion rate are made without relying on any handling or processing of the object 112 during the single run. Determining multiple corrosion rates in the single run when the processing parameters remain unchanged creates redundancy desirable to establish confidence in the corrosion rates determined and to identify any anomaly.

For some embodiments, the corrosion rate determined facilitates characterization of naphthenic acid corrosion given that naphthenic acid structure and species influence corrosiveness. The corrosion rate determined may correspond to the naphthenic acid corrosion independent of sulfidic corrosion. The sulfidic corrosion results in scale formation on the object 112 instead of elution of the metal into the effluent stream 111 due to insolubility of metal sulfide (e.g., FeS) product from the sulfidic corrosion. Determinations for the naphthenic acid corrosion while contact of the object 112 with the liquid is still in progress can provide a pre-indication of the sulfidic corrosion without accessing the object 112 since the naphthenic acid corrosion slows upon buildup of the scale. In some embodiments, at least limiting sulfur content within the liquid that contacts the object 112 ensures no competing reactions with the object 112 when interested in the naphthenic acid corrosion alone. Addition of sufficient acid concentration into the liquid to dissolve the metal sulfide can permit measuring both the sulfidic corrosion and the naphthenic acid corrosion based on the data from the analysis device 104.

Some embodiments permit separate determinations for the sulfidic corrosion and the naphthenic corrosion. Total corrosion includes both the sulfidic corrosion and the naphthenic corrosion and can be determined by weighing the object 112 after washing, cleaning and scraping the object 112 to remove the scale upon completing the run. Contribution in weight loss of the object 112 due to the naphthenic acid corrosion (i.e., Equation 2) corresponds to weight of iron determined to have been in the liquid as measured utilizing the analysis device 104. A remainder of the weight loss from the object 112 hence corresponds to the sulfidic corrosion, which may be expressed in mathematical form as $$\Delta W_{SulfidicCorrosion}=\Delta W_{Total(weighed)}-\Delta W_{NaphthenicAcidCorrosion(Equation\ 2)}. \quad \text{Equation 1}$$

An independent corrosion rate in units of dimension per unit time for the sulfidic corrosion can thus be calculated using the weight loss due to the sulfidic corrosion in calculations such as Equation 3 set forth herein.

Figure 2:
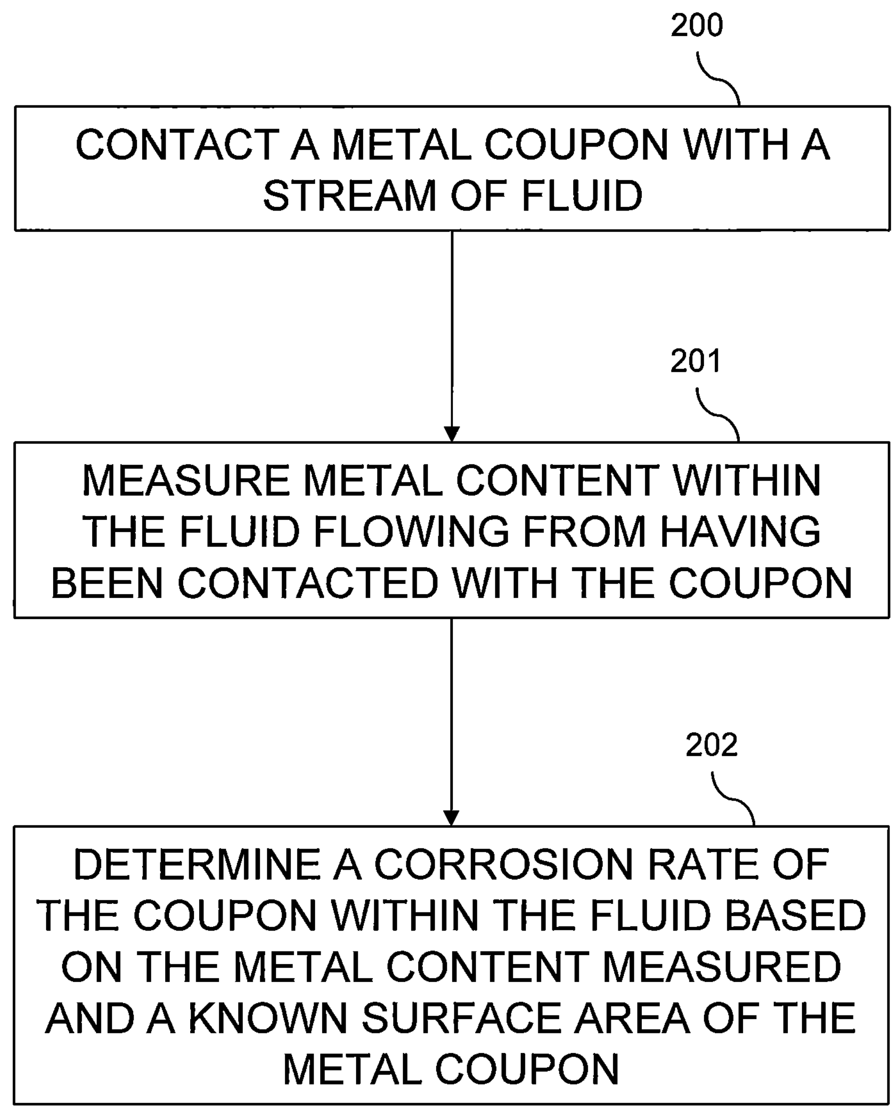
FIG. 2 is a flow chart illustrating a method of measuring corrosion rate based on effluent metal content measured, according to one embodiment of the invention.

FIG. 2 illustrates a flow chart summarizing such a method of measuring corrosion rate based on effluent metal content measured. In reaction step 200, a stream of corrosive fluid contacts a metal coupon. Measuring metal content within the fluid flowing from having been contacted with the coupon occurs in analysis step 201. In a result step 202, determining the corrosion rate of the coupon within the fluid utilizes surface area of the coupon known based on dimensions of the coupon along with the metal content that was measured with the analysis step 201.

EXAMPLES

Table 1 shows results of an experiment. A mixture containing mineral oil and naphthenic acid was passed through an autoclave at a flow rate of 40 milliliters per hour (ml/hr) throughout the experiment. The autoclave contained four carbon steel coupons having dimensions of 2.54 cm×1.27 cm×0.16 cm. Eight samples had respective sample times (hr) with durations determined by when each sample was collected from flow out of the autoclave during the experiment. Sample 1 was taken after heating of the autoclave. Sample 8 represented the mixture remaining in the autoclave at an end of the experiment. Values for iron concentration ([Fe]i) in parts per million (ppm) were obtained for each sample by ICP analysis. Multiplying the flow rate times sample volume and density of the mixture calculated sample weight in grams (g). To obtain iron weight in grams for each sample, the sample weight was divided by one million and multiplied by the iron concentration as shown by $$\Delta W=\sum_{1}^{x}[Fe]i(Sw(i)/10^6). \quad \text{Equation 2}$$

The corrosion rate (K) was calculated in mils per year (mpy; 1 mpy=25.4 microns per year) according to $$K=\frac{(C*\Delta W)}{(D*A*T)}, \quad \text{Equation 3}$$

where C is a conversion constant (~b 530,000), D is density (g/cm$^3$) of the coupons, A is exposed surface area (square inches) of the coupons, and T is time (hr) that the coupons were exposed to the mixture. The density and surface area of the coupons in the experiment were 6.499 square inches (41.93 square centimeters) and 7.86 g/cm$^3$.

TABLE 1

| | Flow (ml/hr) | Sample time (hr) | [Fe]i (ppm) | Sample Volume (ml) | Sample Weight (g) | Fe Weight (g) | Corrosion rate (mpy) |
|---|---|---|---|---|---|---|---|
| Sample 1 | 40 | 2.75 | 31.3 | 110.0 | 93.4 | 0.0029 | n/a |
| Sample 2 | 40 | 2.00 | 158 | 80.0 | 67.9 | 0.0107 | 70.8 |
| Sample 3 | 40 | 13.65 | 223 | 546.0 | 463.6 | 0.1034 | 78.6 |
| Sample 4 | 40 | 2.00 | 215 | 80.0 | 67.9 | 0.0146 | 75.8 |
| Sample 5 | 40 | 2.43 | 217 | 97.3 | 82.6 | 0.0179 | 76.5 |
| Sample 6 | 40 | 1.92 | 217 | 76.7 | 65.1 | 0.0141 | 76.5 |
| Sample 7 | 40 | 1.77 | 214 | 70.7 | 60.0 | 0.0128 | 75.4 |
| Sample 8 | n/a | n/a | 214 | 120.0 | 101.9 | 0.0218 | n/a |
| Total/Cumulative | | | | | | 0.198 | 86.6 |

For comparison, Table 2 shows three separate tests in which the iron weight (ΔW) was calculated utilizing ICP data and was also measured by conventional weighing of coupons before and after each test. Differences in the iron weight calculated with the ICP data and weighed mass loss were less than 2%. Closeness in results proved ability to utilize the iron concentration that is calculated with the ICP data instead of actual weight measurements to obtain the iron weight and hence the corrosion rates, such as depicted in Table 1.

TABLE 2

| | ICP data calculated mass loss (g) | Weighed mass loss (g) |
|---|---|---|
| Test 1 | 0.240 | 0.244 |
| Test 2 | 0.231 | 0.229 |
| Test 3 | 0.204 | 0.200 |

The preferred embodiment of the present invention has been disclosed and illustrated. However, the invention is intended to be as broad as defined in the claims below. Those skilled in the art may be able to study the preferred embodiments and identify other ways to practice the invention that are not exactly as described herein. It is the intent of the inventors that variations and equivalents of the invention are within the scope of the claims below and the description, abstract and drawings are not to be used to limit the scope of the invention.

What is claimed is:

1. A method comprising: exposing an object made of metal to a flow of corrosive liquid, wherein the object has measurable dimensions such that the object may be subjected to direct measurement for determining a known surface area;

determining the known surface area of the object from the measurable dimensions;

withdrawing an effluent stream from the flow of said corrosive liquid after exposure of the object to the corrosive liquid;

passing said effluent stream such that the effluent stream includes a concentration of metal from said object into an analysis device to determine a concentration of the metal within the effluent stream after the object is exposed to the corrosive liquid; and determining a corrosion rate of the metal within the effluent stream based on the known surface area of the object and the concentration of the metal within effluent stream as measured by the analysis device, wherein the corrosion rate is determined for each of two distinct time intervals independent from one another and without opening an autoclave in which the object is disposed and for each of two distinct time intervals having different processing parameters from one another.

2. The method according to claim 1, further comprising determining a separate rate for sulfidic corrosion of the metal within the corrosive liquid, wherein the corrosion rate corresponds to naphthenic acid corrosion independent of the sulfidic corrosion.

3. The method according to claim 1, wherein the corrosion rate is based on a summation of metal weight calculated from the concentration of the metal measured in multiple samples of the effluent stream.

4. The method according to claim 1, wherein the corrosion rate has units of dimension per period of time.

5. The method according to claim 1, wherein the corrosive liquid includes naphthenic acid.

6. The method according to claim 1, wherein the metal includes iron.

7. The method according to claim 1, wherein the analysis device measures the concentration of the metal by inductively coupled plasma atomic emission spectroscopy.

8. The method according to claim 1, further comprising disposing the object within a heated interior of an autoclave where the object is exposed to the flow of the corrosive liquid above ambient pressure.

9. The method according to claim 1, wherein the corrosion rate corresponds to naphthenic acid corrosion independent of sulfidic corrosion.

10. The method according to claim 1, wherein the passing of the effluent stream into the analysis device includes measuring the concentration of the metal within a first sample of the effluent stream during a first time interval and a second sample of the effluent stream during a second time interval after the first time interval so as to determine the corrosion rate for each of the time intervals independent from one another.

11. The method according to claim 1, further comprising providing a computer with logic stored on computer readable memory and configured to perform the determining of the corrosion rate.

12. The method according to claim 1, further comprising transmitting the corrosion rate to an output that provides the corrosion rate to a user.

13. The method according to claim 1, wherein the corrosion rate (K) is calculated according to $$K = \frac{(C * \Delta W)}{(D * A * T)} \text{ and } \Delta W = \sum_{1}^{x} [Fe]i(Sw(i)/10^6),$$

where C is a conversion constant, D is density of the object, A is the surface area of the object, T is time that the object is exposed to the corrosive liquid, x is number of samples of the effluent stream collected, [Fe] is concentration of iron in sample i, and Sw(i) is weight of the effluent stream that produced sample i.

14. A method comprising:

preparing an autoclave for operation, wherein the preparing includes closing the autoclave for internal pressurization of the autoclave above ambient pressure and heating the autoclave to a reaction temperature;

exposing an object made of metal and disposed in the autoclave to a flow of corrosive liquid passing through the autoclave, wherein the object has measurable dimensions such that the object may be subjected to direct measurement for determining a known surface area;

withdrawing an effluent stream from the flow of corrosive liquid after exposure of the object to the corrosive liquid;;

passing into an analysis device a first sample of the effluent stream taken from the autoclave during a first time interval;

passing into the analysis device a second sample of the effluent stream taken from the autoclave during a second time interval after the first time interval, wherein the first and second samples are obtained without removing the object from the autoclave that remains closed;

determining a concentration of the metal within the first and second samples of the effluent stream; and determining corrosion rates of the metal within the effluent stream for the first and second time intervals independent from one another, wherein the corrosion rates are based on the known surface area of the object and the concentrations of the metal within the effluent streams of the first and second samples as measured by the analysis device.

15. The method according to claim 14, wherein a hydrocarbon and naphthenic acid mixture forms the corrosive liquid and the metal includes iron and defines a singular continuous mass with the known surface area that is greater than about 5 square centimeters.

* * * * *